United States Patent [19]

Sparks

[11] 3,931,350
[45] Jan. 6, 1976

[54] PROCESS FOR PRODUCING ALKYLAROMATICS

[75] Inventor: Allen K. Sparks, Des Plaines, Ill.

[73] Assignee: Universal Oil Products Company, Des Plaines, Ill.

[22] Filed: Mar. 25, 1974

[21] Appl. No.: 454,626

Related U.S. Application Data

[60] Division of Ser. No. 265,092, June 21, 1972, Pat. No. 3,848,006, which is a continuation-in-part of Ser. No. 803,057, Feb. 27, 1969, abandoned.

[52] U.S. Cl............. 260/671 B; 208/266; 208/268; 208/279; 260/676 R; 260/676 AD; 260/676 MS
[51] Int. Cl.$^2$.......................................... C07C 3/52
[58] Field of Search ..... 260/671 B, 676 R, 676 AD, 260/676 MS; 208/266, 268, 279

[56] References Cited
UNITED STATES PATENTS

| | | | |
|---|---|---|---|
| 1,820,907 | 9/1931 | Buc | 208/279 |
| 2,170,620 | 8/1939 | Skrepinsky | 208/268 |
| 2,257,914 | 10/1941 | Morley | 208/263 |
| 2,628,933 | 2/1953 | Eagle et al. | 260/676 |
| 3,365,508 | 1/1968 | Kapur et al. | 260/671 |
| 3,394,200 | 7/1968 | Sargent | 260/676 |
| 3,403,194 | 9/1968 | Feighner et al. | 260/671 |

Primary Examiner—Delbert E. Gantz
Assistant Examiner—C. E. Spresser
Attorney, Agent, or Firm—James R. Hoatson, Jr.; Thomas K. McBride; William H. Page, II

[57] ABSTRACT

In a process for producing alkylaromatics by halogenating a paraffin and reacting the halogenated paraffin with an aromatic hydrocarbon, the rate of halogenation is improved by treating the n-paraffin to selectively remove oxygen-containing hydrocarbonaceous compounds from the n-paraffin with a sorbent selective for such oxygen-containing compounds, and subsequently halogenating the treated n-parffin. The improvement is particularly useful in producing alkylaromatic hydrocarbons from monocyclic aromatic compounds and n-paraffins.

3 Claims, No Drawings

PROCESS FOR PRODUCING ALKYLAROMATICS

CROSS-REFERENCES TO RELATED APPLICATIONS

This application is a division of my copending application Ser. No. 265,092, filed on June 21, 1972, now U.S. Pat. No. 3,848,006, Nov. 12, 1974, which is, in turn, a continuation-in-part of my copending application Ser. No. 803,057, filed on Feb. 27, 1969, now abandoned, the teachings of both of which are incorporated herein by specific reference.

BACKGROUND OF THE INVENTION

This invention relates to the mono-chlorination or monobromination of a $C_9$–$C_{18}$ n-paraffin to produce an alkylating agent. In one aspect, this invention relates to a process for producing an alkyl-aromatic by monohalogenating a $C_9$–$C_{18}$ n-paraffin and alkylating an aromatic with the monohalogenated n-paraffin to provide an alkylaromatic intermediate in detergent alkylate production. More specifically, this invention relates to the removal of oxygen-containing hydrocarbonaceous compounds formed by the oxidation of a $C_9$–$C_{18}$ n-paraffin, which oxygen-containing compounds, when present in admixture with the n-paraffin, inhibit the rate of halogenation of the paraffin. This invention further relates to an improved process for producing an alkylaromatic product from a $C_9$–$C_{18}$ normal paraffin and a monocyclic aromatic.

Processes for the production of straight chain alkylaromatics have gained considerable importance in the past few years as a result of the demand for control of water pollution. The relevant alkylaromatics are those having an aromatic nucleus bonded at various positions on a linear alkyl chain to a $C_9$–$C_{18}$ linear alkyl group. When such alkylaromatics are converted to detergents through sulfonation, neutralization, etc., the resulting detergent is more bio-degradable than a detergent of the same chemical composition in which the alkyl chain is highly branched, e.g., detergents prepared from propylene tetramer.

A preferred method for preparing the bio-degradable detergents includes mono-chlorinating or mono-brominating a $C_9$–$C_{18}$ n-paraffin to form the corresponding mono-halogenated paraffin. The mono-halogenated paraffin is employed as an alkylating agent and is reacted with a monocyclic aromatic, typically benzene, to form the desired biodegradable detergent alkylate precursor.

In mono-halogenating paraffins for use in preparing alkylaromatics, thermal halogenation is preferred over halogenation processes utilizing a catalytic agent. Halogenation processes in which a catalyst is employed typically produce di- or polyhalogenated paraffins in excessive quantities and also produce olefins, which are highly undesirable in a mono-halogenation operation. Thermal halogenation has been found to provide a more selective and easily controllable method of halogenation, giving a higher yield of the desired mono-halogenated paraffins, while producing fewer undesirable side products. Thermal halogenation is also generally preferred because the thermal route obviates the difficulties and expense inherent in handling a catalyst. For example, the presence of water, aromatics and other contaminants is known to have a deleterious effect on halogenation catalysts, and therefore halogenation processes using such catalysts must make provisions for removal of such contaminants. This leads to further complication and expense.

One of the continuing goals in the halogenation art is to increase the rate of halogenation while maintaining the selectivity of the process for producing monohalogenated paraffins, in contrast to di- and polyhalogenated paraffins or olefins. This is particularly true where the halogen employed is bromine. Bromine is known to react slowly with n-paraffins as compared to chlorine, for example. In many cases, however, bromine is preferred over chlorine as a halogenation agent, since the hydrogen bromide formed in the halogenation reaction is more easily converted to molecular bromine than is hydrogen chlorine converted to molecular chlorine. Since molecular bromine and chlorine are the halogenation agents normally used in such a halogenation process, it is preferred to use bromine rather than chlorine so that recycle of the halogen is facilitated. Prior art recognition that n-paraffins are relatively difficult to halogenate has led to the use of halogenation processes to selectively halogenate and separate isoparaffins from n-paraffins.

I have made the surprising discovery that when the paraffin employed in thermal halogenation contains oxygen-substituted hydrocarbonaceous compounds, such as those formed by air oxidation of a normal paraffin, the oxygen-containing compounds act as inhibitors in the halogenation reaction, even when present in small amounts. The resulting slower rate of reaction necessitates the use of a larger reactor, longer reaction time, etc., and thereby results in undesirable additions to the expense and complication of the operation of a halogenation process.

SUMMARY OF THE INVENTION

It is, therefore, an object of this invention to provide a method for improving the rate of halogenation of a $C_9$–$C_{18}$ n-paraffin. A further object of this invention is to provide an efficient process for the production of alkylaromatics suitable for use in production of biodegradable detergents using an n-paraffin reactant and an aromatic reactant.

In an embodiment, the present invention relates to an improved process for the halogenation of a feed stock containing a $C_9$–$C_{18}$ n-paraffin by reaction with chlorine or bromine, wherein oxygen-containing hydrocarbonaceous compounds are present in said feed stock in concentrations sufficient to inhibit the rate of halogenation of said n-paraffin, the improvement which comprises contacting said feed stock, prior to said halogenation, with a sorbent capable of selectively removing said oxygen-containing compounds from said feed stock, under separation conditions sufficient to remove at least a portion of said oxygen-containing compounds from said feed stock, whereby the rate of halogenation of said n-paraffin is increased.

In another embodiment, the present invention relates to an improved process for producing an alkylaromatic product from an alkylatable monocyclic aromatic compound and a feed stock containing a $C_9$–$C_{18}$ n-paraffin by halogenating said n-paraffin with chlorine or bromine to provide an alkyl mono-halide alkylating agent and alkylating said aromatic with said alkylating agent to provide said alkyl-aromatic product, wherein oxygen-containing hydrocarbonaceous compounds are present in said feed stock at concentrations sufficient to inhibit the rate of halogenation of said n-paraffin, the improvement which comprises contacting said feed stock, prior to said halogenation, with a sorbent capable of selectively removing said oxygen-containing compound, under separation conditions sufficient to remove at least a portion of said oxygen-containing compounds from said feed stock, whereby the rate of halogenation of said n-paraffin is increased.

Through the use of the improvement of the present invention, the rate of halogenation of a $C_9$–$C_{18}$ n-paraffin having oxygen-containing hydrocarbonaceous impurities therein is greatly increased by the removal of these oxygen-containing impurities. A more efficient process for the production of an alkylaromatic detergent precursor through mono-halogenation of a $C_9$–$C_{18}$ normal paraffin and alkylation of a monocyclic aromatic with the resulting mono-halogenated paraffin is thereby provided.

DESCRIPTION OF THE PREFERRED EMBODIMENTS

The $C_9$–$C_{18}$ normal paraffins utilized in the improved process of this invention include n-nonane, n-decane, n-octadecane, etc., and mixtures thereof. Such normal paraffins may be obtained from any suitable source including an appropriate fraction of a straight-run petroleum distillate, such as the kerosene fraction. The normal paraffins may also be obtained as a product of the Fisher-Tropsch reaction, a process by which paraffinic hydrocarbons in the $C_9$–$C_{18}$ range are formed by the reaction of hydrogen with carbon monoxide. Similarly, the hydrogenated products of ethylene polymerization and hydrogenated fatty acids, which, upon complete hydrogenation, produce paraffinic hydrocarbons have a straight chain configuration, may be employed. Although any suitable source may be used to supply the feed stock containing the $C_9$–$C_{18}$ normal paraffins utilized in the present process, the preferred source of the normal paraffin feed stock is a petroleum distillate fraction boiling in the range from about 170° C. to about 300° C., which contains the desired $C_9$–$C_{18}$ normal paraffins.

Most of the sources of the feed stock described above also contain a significant amount of branched chain $C_9$–$C_{18}$ isomers in admixture with the normal paraffins. These branched isomers must be separated from the feed stock if the n-paraffins are to be utilized as reactants in the preparation of linear alkylbenzenes. The normal paraffins may be separated from the branched isomers by any of the procedures known in the art, the exact method of separation of the normal paraffin-containing feed stock not being critical to the present invention. Such processes may include, for example, the use of molecular sieve sorbents or adduction with clathrate-forming compounds such as urea.

A preferred method of separation is by the use of molecular sieve sorbents. The preferred molecular sieves of this type are characterized by their chemical compositions as a dehydrated metal aluminosilicates having a zeolite crystal structure and containing pore openings about 5 Angstroms in cross-sectional diameter which are of sufficient size to permit the entry of normal paraffinic compounds but are not of sufficient size to permit the entry of branched chain or cyclic compounds in the same boiling range. The use of such molecular sieves to separate normal hydrocarbons is well known. For example, a process for the separation of normal hydrocarbons using molecular sieves which can be employed to provide a suitable feed stock may be found in U.S. Pat. No. 2,920,037. Another suitable method for separating the normal paraffins may be found in U.S. Pat. No. 2,957,927. The concept of the use of moving inlets and outlets to simulate countercurrent flow of the molecular sieves and using zeolites is also well known. An example of a suitable process using such an operation is disclosed in U.S. Pat. No. 2,985,589. These processes include the use of a hydrocarbonaceous desorbent which is generally outside the molecular weight and boiling range of the feed stock to be separated. Critical factors in such separation operations are the rate of sorption of the selectively sorbed molecules and the selectivity of the molecular sieve sorbent for the selectively sorbed molecules. If the rate of sorption is slow, or if the selectivity of the sorbent for the preferentially adsorbed molecules is low, the overall amount of extraction of the desired n-paraffins will be low. When the feed stock to be separated is a heavier feed stock, for example, in the kerosene boiling range such as the feed stock of the present process, the rate of sorption may indicate that the use of operations which are described in U.S. Pat. No. 3,306,848 would also be beneficial.

Irrespective of the method used to provide the feed stock containing the $C_9$–$C_{18}$ n-paraffin, according to the process of the present invention, the $C_9$–$C_{18}$ n-paraffins in the feed stock are mono-halogenated with bromine or chlorine to provide mono-halogenated paraffins. Various methods for effecting the mono-halogenation are known in the art, including catalytic and non-catalytic methods. In general, catalytic halogenation is more suitable for producing di- and poly-halogenated paraffins, while non-catalytic or thermal halogenation is more suitable for producing mono-halogenated paraffins. In general, mono-halogenation is effected by contacting the feed stock containing $C_9$–$C_{18}$ n-paraffins with molecular chlorine or bromine at a halogen/paraffin mole ratio of about 0.05 to about 0.5. The mono-halogenation step may be performed in a vapor phase operation or a liquid phase operation. Radiation, trace amounts of iodine, or other known catalysts may be employed if desired. Such catalysts and their use in conventional mono-halogenation operations are known in the prior art. The feed stock may contain a single suitable n-paraffin, e.g., n-dodecane, or may suitably contain a mixture of two or more $C_9$–$C_{18}$ n-paraffins. A preferred method for undertaking the halogenation step is by reacting the paraffin in the liquid phase and molecular halogen at a temperature of about 50° C. to about 400° C., preferably from about 75° C. to about 250° C. The mono-halogenation may be performed in a batch-type operation or in a continuous operation. In general, any conventional method suitable for providing a mono-halogenated $C_9$–$C_{18}$ n-paraffin from a $C_9$–$C_{18}$ n-paraffin feed stock and a molecular halogen consisting of bromine or chlorine may be employed in the present process.

In accordance with the improved process of the present invention, I have found that when certain oxygen-containing hydrocarbonaceous compounds are present in the n-paraffin feed stock to be utilized in a halogenation operation, these oxygen-containing compounds severely inhibit the rate of reaction between the halogen and paraffin to form the desired halogenated n-paraffin. It is known that aromatic hydrocarbons, when present in the n-paraffin feed stock, may adversely effect the halogenation operation by reacting with the relatively expensive halogen, thus requiring an undesirably large halogen supply. It has also been found previously that water may adversely effect the operation of some halogenation catalysts, thereby reducing the rate of halogenation in an operation employing such catalysts. However, it has not heretofore been determined that the presence of oxygen-containing hydrocarbonaceous compounds in the n-paraffin feed stock has a severe adverse effect on the rate of halogenation, and, in particular, this adverse effect is evidenced in a conventional thermal mono-halogenation operation. I have found that this inhibition of the rate of halogenation is dependent on the concentration of the undesirable oxygen-containing hydrocarbonaceous compounds in the n-paraffin feed stock and is not substantially effected by the presence or absence of small, conventional amounts of aromatic hydrocarbons or water in the feed stock. The undesirable oxygen-containing hydrocarbonaceous compounds particularly include, but are not limited to, those compounds formed by reaction of a $C_9$–$C_{18}$ n-paraffin with oxygen. For example, I have found that $C_9$–$C_{18}$ n-paraffin feed stocks, initially free from oxygen-containing hydrocarbonaceous compounds, when exposed to air for any substantial period, will react to form $C_9$–$C_{18}$ oxygen-containing compounds in concentrations which are relatively small but are sufficient to severely inhibit the rate of reaction in a halogenation operation. The undesirable oxygen-containing compounds comprise carbonyl- and hydroxyl-containing hydrocarbonaceous compounds. The undesirable effect of these compounds is evident when their concentration in the n-paraffin feed stock is as low as 0.01 wt. %, or less, even trace amounts causing some impairment. The inhibitory effect is very strong when the oxygen-containing compounds are present at concentrations of about 0.05 wt. percent or greater.

It will be apparent to those skilled in the art that limitations as to the effective concentration of undesirable oxygen-containing hydrocarbonaceous compounds in a $C_9$–$C_{18}$ n-paraffin feed stock are not essential to an understanding of the operation and utility of the present invention. The present invention concerns an improvement in a process for halogenating a $C_9$–$C_{18}$ n-paraffin feed stock. Conventionally, such a feed stock contains minor amounts of various contaminants such as aromatics, water, etc. Since a conventional feed stock will generally have been exposed to air one or more times for possibly substantial periods, in conventional operations, before being used in a halogenation operation, it will generally be the case in such a conventional operation that small amounts, e.g., 0.01 to 0.1 wt. % of the oxygen-containing hydrocarbonaceous impurities, sufficient to adversely effect halogenation, will be present in a conventional feed stock. Thus, the present invention is primarily directed to embodiments wherein a conventional n-paraffin feed stock, containing small amounts of such impurities, is treated to remove the impurities. The present invention is not limited to such embodiments, however, and can, if desired, be employed to treat $C_9$–$C_{18}$ n-paraffin feed stocks containing any amount of the undesirable compounds. Similarly, it will be apparent that the improved process of the present invention can be applied in the halogenation of other hydrocarbon feed stocks besides the preferred $C_9$–$C_{18}$ n-paraffin feed stock if such is found desirable. The use of such other feed stocks or the use of feed stocks in which oxygen-containing hydrocarbonaceous compounds are present in concentrations outside the range from about 0.001 to 1.0 wt. %, for example, may not necessarily lead to results equivalent to the results obtained using the preferred feed stocks.

The undesirable oxygen-containing compounds are removed from the n-paraffin feed stock prior to the halogenation step by contacting the feed stock with a sorbent which selectively removes the impurities from the feed stock without otherwise modifying the n-paraffin. The useful sorbents are, therefore, those which are substantially inert toward $C_9$–$C_{18}$ n-paraffins at the temperatures and contact times necessary to effect removal of the oxygen-containing compounds. At the same time, a useful sorbent must be capable of selectively absorbing or adsorbing the impurities without absorbing or adsorbing any substantial amount of the n-paraffins. A suitable liquid sorbent must be substantially immiscible with the feed stock to prevent separation problems. I have found that some mineral acid, including particularly sulfuric acid and phosphoric acid, are suitable for use as a sorbent in the separation step. These preferred acids are preferably used in concentrations of about 80 wt. % or more and preferably contain less than about 20 wt. % water. Acids such as nitric acid which may react with hydrocarbons to a substantial extent should not be employed. Other acids which are not suitable, either because they are miscible with the n-paraffins to too great an extent or because they cannot selectively remove the impurities, include, for example, carboxylic acids and the hydrogen halides.

When a liquid sorbent is employed, the sorbent and feed stock are contacted at a sorbent/feed stock volume ratio of about 0.01:1 to about 2:1. Preferably, the sorbent and feed stock are thoroughly admixed, e.g., by agitation, stirring, etc., in order to insure effective contact between the sorbent phase and the hydrocarbon phase, which aids in the removal of the oxygen-containing compounds from the feed stock. When using the preferred liquid sorbents, sulfuric acid and phosphoric acid, suitable contact times are in the range from about one minute to about twenty-four hours or more. Generally, when these preferred sorbents are employed, a shorter contact time will be required when a higher sorbent/feed stock volume ratio is used. Similarly, when the sulfuric acid or phosphoric acid is more concentrated, e.g., 90 wt. % acid, as contrasted with a weaker 80 wt. % acid, a shorter contact time and/or lower sorbent/feed stock volume ratio is used, with good results in separating the impurities. The sorbent and feed stock can be contacted in a batch operation wherein the desired volumes of sorbent and feed stock are placed in an appropriate vessel, contacted for a time sufficient to remove the impurities from the feed stock, preferably with agitation, stirring, etc., and/or heating, and the feed stock is subsequently separated from the sorbent and passed to the halogenation step. Similarly, the sorbent may be contacted with the feed stock in a continuous type operation through either co-current or countercurrent contact.

As will be obvious to those skilled in the art, when the preferred liquid sorbents, i.e., sulfuric acid and phosphoric acid, are employed, it may be desirable to treat the feed stock after the separation step, e.g., by washing with water and/or an aqueous alkaline solution. Such a procedure is not essential to the present process, but may be desirable to avoid acid contamination of the feed stock. Means and methods for performing such a washing or neutralization operation are well known to those skilled in the art.

When a solid sorbent is employed, the sorbent and feed stock are contacted at a liquid hourly space velocity (defined as the volume of feed stock contacted with the sorbent per hour per volume of sorbent) of about 0.1 per hour to about 10.0 per hour or more. The sorbent may be employed as a fixed bed in a suitable vessel and the feed stock continuously passed into the vessel, contacted with the sorbent, withdrawn, and passed to the halogenation operation. A batch operation may also be employed, wherein a quantity of sorbent and feed stock are placed in a vessel, contacted for a predetermined period, preferably with agitation or stirring, and then separated. Other suitable methods of employing a solid sorbent include co-current and countercurrent contact between the sorbent and feed stock on a continuous basis. The preferred method of performing the separation step using a solid sorbent is by employing the sorbent as a fixed bed and continuously passing the feed stock over the bed. The preferred solid sorbents are dehydrated silica gel and activated alumina. Other suitable solid sorbents, which may not give results equivalent to those found using the preferred solid sorbents, include activated charcoal, zeolites, clay, etc. The sorbent may be used as a solid mass, but is preferably in the form of small diameter pellets or spheres. Also included as a suitable solid sorbent is a sulphonic ion-exchange resin.

Irrespective of the particular method used to effect the removal of the undesirable oxygen-containing hydrocarbonaceous compounds from the $C_9$–$C_{18}$ n-paraffin feed stock, the feed stock is subsequently halogenated as described above and passed to the alkylation step. In the alkylation step, the mono-halogenated n-paraffin is alkylated with a monocyclic aromatic compound to yield a linear alkylaromatic compound suitable for use in preparing a bio-degradable detergent. The monocyclic aromatic compounds which are to be alkylated with the olefin-acting mono-halogenated paraffin to yield the linear alkylaromatic include benzene, toluene, xylene, ethylbenzene, diethylbenzene, and phenol. The alkylation reaction is effected in the presence of a suitable catalyst. Such catalysts, suitable for use in the alkylation step of the present process, include acid-acting compounds which catalyze the alkyl transfer reaction. Such compounds include certain mineral acids such as sulfuric acid preferably containing less than 10% water, hydrofluoric acid of at least 80% concentration and containing preferably less than 10 wt. % water, liquefied anhydrous hydrogen fluoride, anhydrous aluminum chloride or aluminum bromide, boron trifluoride, preferably utilized in admixture with hydrogen fluoride, and other similar acid-acting catalysts, particularly of the Friedel-Crafts class of metal halides.

The preferred Friedel-Crafts catalyst for use in alkylation of the mono-halogenated paraffin with the suitable monocyclic aromatics is aluminum chloride. The aluminum chloride catalyst is used in a concentration of about 1 wt. % to about 20 wt. % of the amount of mono-halogenated paraffin present during the alkylation operation. The catalyst may be utilized directly as a salt or may be employed as an acid sludge obtained from previous alkylation operations. Preferred alkylation conditions include temperatures from about 30° C. to about 90° C. A molar excess of the monocyclic aromatic is normally utilized in the alkylation operation to avoid the formation of di-alkylbenzenes. The molar excess of aromatic may vary from about 2:1 up to about 20:1, with a ratio of about 3:1 to about 10:1 being preferred. Reaction times employed are from about 10 minutes up to about 100 minutes. As is well known in the art, the exact reaction time employed, concentration of the catalyst, etc., are interdependent and reference may be made to the prior art for teachings as to specific processing details.

Upon completion of the alkylation reaction, the hydrocarbons are preferably washed with an aqueous caustic solution such as 10% sodium hydroxide in water, and unreacted monocyclic aromatic, unconverted paraffin, and product linear alkylate are recovered and separated by means well known to the art such as, for example, fractional distillation. Preferably, the unreacted monocyclic aromatic compounds and the unconverted $C_9$–$C_{18}$ n-paraffins are recycled to the particular steps in the process in which they are employed in order to obtain the maximum utilization of these reactants in the process. The $C_9$–$C_{18}$ n-paraffins recycled to the halogenation step can be contacted with the same type of sorbent utilized in treating the fresh paraffin feed stock before passing the feed stock to the halogenation step. The recycled normal paraffins may be combined with fresh feed stock of $C_9$–$C_{18}$ n-paraffins or may be treated separately and later combined with the treated fresh feed stocks and passed to the halogenation operation. Treatment of the recycle paraffins can serve several purposes. It removes any undesirable oxygen-containing compounds formed by oxidation of the $C_9$–$C_{18}$ n-paraffins which may have been formed during the halogenation and alkylation operation and which will inhibit the halogenation reaction. Treatment of the recycle paraffins will also remove trace amounts of aromatics present in the paraffin stream and not removed by separation operations such as fractional distillation. The aromatics, if present in the halogenation reaction, will result in excessive consumption of the halogen.

The following examples are presented in order to illustrate the utility of the present invention and to illustrate some of the preferred embodiments of the improved process of the present invention. The scope of the invention is not limited to the examples presented, and no limitations as to the scope and possible embodiments of the present process are to be implied therefrom.

EXAMPLE I

A supply of n-dodecane feed stock was obtained and analyzed. It was found to have the following composition:

| Component | Wt. % |
|---|---|
| n-dodecane | 95.75 |
| n-undecane | 0.8 |
| n-tridecane | 0.09 |
| n-decane | trace |
| isoparaffins | 2.60 |
| aromatics | 0.65 |
| —OH | 0.01 |
| C=O | 0.05 |

A portion of the n-dodecane feed stock was mixed with a portion of 96 wt. % sulfuric acid at a 5:1 hydrocarbon to acid volume ratio in an alkylation flask. The mixture was stirred vigorously and maintained at a temperature of 90°–110° C. for 2 hours. The mixture was then cooled and allowed to separate into a hydrocarbon layer and an acid layer. The hydrocarbon layer was recovered and washed with a volume of water equal to about 20 vol. % of the hydrocarbons. The washing procedure was repeated with a 10 mole % NaOH solution and again with water. The hydrocarbon was then dried using $Na_2SO_4$ and stored under a nitrogen atmosphere. This treated hydrocarbon was analyzed and found to have the following composition:

| Component | Wt. % |
|---|---|
| n-dodecane | 95.84 |
| n-undecane | 0.81 |
| n-tridecane | 0.09 |
| n-decane | trace |
| isoparaffins | 2.60 |
| aromatics | 0.65 |
| —OH | none |
| C=O | none |
| water | 100 ppm |

851 grams of the treated hydrocarbon was used in a bromination procedure as follows: The hydrocarbon was placed in an alkylation flask fitted with a stirrer and heated to 66° C. 0.05 mole of reagent grade bromine was pipetted rapidly into the flask with stirring and the flask stoppered immediately. Samples were withdrawn periodically and reaction quenched by immersion in an ice-salt bath at −10° C. to −15° C. The samples were brought to room temperature and an aliquot portion was pipetted into an iodine flask containing 50 cc. of deionized water and 5 cc. of 1.0M KI solution. The iodine was then titrated with $0.1N\ Na_2S_2O_3$ with soluble starch indicator to determine the bromine content. The reaction rate between the hydrocarbon and bromine in the alkylation flask was determined and assigned the arbitrary comparitive value of 30.

EXAMPLE II

The rate of bromination of the untreated n-dodecane feed stock was compared to the rate of bromination of the same feed stock after treatment in accordance with the present invention as described in Example I. This was done as follows: 85.1 grams of the untreated n-dodecane feed stock having the composition stated in Example I was employed in the exact same bromination procedure as used in Example I. The reaction rate of the untreated n-dodecane feed stock was found to have a value of 1 as compared to the value of 30 for the reaction rate of the sorbent-treated hydrocarbon in Example I.

EXAMPLE III

A second supply of n-dodecane was obtained and analyzed to determine its composition, which was found to be as follows:

| Component | Wt. % |
|---|---|
| n-dodecane | 99.8 |
| isoparaffins | trace |
| other n-paraffins | trace |
| aromatics | 0.008 |
| —OH | 0.05 |
| C=O | 0.05 |

A portion of this feed stock was employed in the new bromination procedure in order to determine the effect of aromatics on the rate of bromination. 85.1 grams of this n-dodecane feed stock containing 0.008 wt. % aromatics was employed in the exact same bromination procedure as used in Example I. The bromination rate of this feed stock was found to have a value of 1 relative to the value of 30 for the sorbent-treated hydrocarbon in Example I.

EXAMPLE IV

In order to determine the effect of the water concentration on the rate of bromination of the normal paraffin, the following procedure was employed. A portion of the untreated n-dodecane feed stock as described in Example I was distilled over sodium metal in order to remove all the water. The distilled material was analyzed and found to have the following composition:

| Component | Wt. % |
|---|---|
| n-dodecane | 95.75 |
| n-undecane | 0.8 |
| n-tridecane | 0.09 |
| n-decane | trace |
| isoparaffins | 2.6 |
| aromatics | 0.65 |
| —OH | none |
| C=O | 0.10 |
| water | none |

851 grams of the distilled hydrocarbons, containing no detectable water, was employed in the exact same bromination procedure as used in Example I. The bromination rate of this water-free n-paraffin feed stock was found to have a value of 1 relative to the value of 30 for the sorbent-treated hydrocarbon brominated in Example I. It was, thus, clearly demonstrated that the water content had no effect whatsoever on the rate of bromination.

EXAMPLE V

In order to demonstrate the effectiveness of a solid sorbent in the present improved bromination process, the following procedure was employed: A portion of the untreated n-dodecane feed stock used in Example I and having the composition shown therein was obtained and passed through a column of dehydrated silica gel at a space velocity (defined as volume of feed stock passed per hour per volume of silica gel) of about 4 per hour. The silica gel-treated feed stock was stored under nitrogen and a portion was removed and analyzed. The composition was found to be as follows:

| Component | Wt. % |
|---|---|
| n-dodecane | 96.45 |
| n-undecane | 0.8 |
| n-tridecane | 0.1 |
| n-decane | trace |
| isoparaffins | 2.64 |
| aromatics | trace |
| —OH | none |
| C=O | trace |

Subsequently, 85.1 grams of the gel-treated feed stock was employed in the exact same bromination procedure as used in Example I. The bromination rate was found to have a value of 13 as compared to the value of 30 for the sulfuric acid-treated feed stock and the value of 1 for the untreated feed stock.

I claim as my invention:

1. In a process for producing a linear alkylaromatic product from a $C_9$–$C_{18}$ n-paraffin-containing feed stock and a monocyclic aromatic hydrocarbon by (i) contacting said $C_9$–$C_{18}$ n-paraffin-containing feed stock with chlorine or bromine in a halogenation step to form a monohalogenated n-paraffin alkylating agent, and (ii) reacting said aromatic hydrocarbon with said alkylating agent in an alkylation step, utilizing an alkylation catalyst, to provide said linear alkylaromatic product, wherein oxygen-containing hydrocarbonaceous compounds are present in said feed stock in concentrations sufficient to inhibit the rate of halogenation of said n-paraffin in said halogenation step, the improvement which comprises contacting said feed stock, prior to said halogenation step, with a sorbent selected from the group consisting of dehydrated silica gel, activated alumina, activated charcoal, zeolites, clay and sulphonic ion-exchange resin under separation conditions, including a contact time of about 0.1 to about 120 minutes and a temperature of about 0° C. to about 200° C., sufficient to remove at least a portion of said oxygen-containing compounds from said feed stock, whereby the rate of halogenation of said n-paraffin is increased.

2. The improvement of claim 1 wherein said sorbent is dehydrated silica gel.

3. The improvement of claim 1 wherein said sorbent is activated alumina.

* * * * *